United States Patent [19]

Branstetter et al.

[11] Patent Number: 4,796,636

[45] Date of Patent: Jan. 10, 1989

[54] NONINVASIVE REFLECTANCE OXIMETER

[75] Inventors: Ronald L. Branstetter; Reuben W. Edgar, Jr., both of San Antonio, Tex.

[73] Assignee: Nippon Colin Co., Ltd., Komaki, Japan

[21] Appl. No.: 95,125

[22] Filed: Sep. 10, 1987

[51] Int. Cl.⁴ .............................................. G01N 33/48
[52] U.S. Cl. ...................................... 128/633; 356/42
[58] Field of Search .................. 128/633, 691; 356/41, 356/42

[56] References Cited

U.S. PATENT DOCUMENTS

| | | | |
|---|---|---|---|
| 4,407,290 | 10/1983 | Wilber | 128/633 |
| 4,446,871 | 5/1984 | Imura | 128/633 |
| 4,447,150 | 5/1984 | Heinemann | 356/41 |
| 4,623,248 | 11/1986 | Sperinde | 128/634 X |
| 4,641,658 | 2/1987 | Lepper | 356/39 X |
| 4,651,741 | 3/1987 | Passafaro | 356/41 X |
| 4,694,833 | 9/1987 | Hamaguri | 356/41 X |

*Primary Examiner*—William E. Wayner
*Attorney, Agent, or Firm*—Hamilton, Smith & Clarkson

[57] ABSTRACT

A noninvasive optical oximeter for measuring oxygen saturation of arterial blood. A sample of blood is illuminated with light at two different wavelengths. Light reflected by the blood is sensed by a photodetector and an output signal is created in response thereto. The output signal is processed to form a quotient representing the AC components of the reflected light at each wavelength. The oxygen saturation of the blood is calculated by correlating this quotient with an oxygen saturation reference curve uniquely representative of the blood oxygen saturation characteristics of a particular individual. The reference curve used in the preferred embodiment of the invention is calibrated in a two-step process which minimizes the effects of calibration errors. A first oxygen saturation reference curve is calculated which is based on a linear relationship between the ratio of the AC components of the reflected light. This curve is then used to calibrate a second reference curve based on a linear ratio of the squared values of the AC components of the reflected light. Once the second reference curve has been properly calibrated, it is used for all subsequent measurements of oxygen saturation.

18 Claims, 3 Drawing Sheets

NONINVASIVE REFLECTANCE OXIMETER

FIELD OF THE INVENTION

The present invention relates generally to monitoring equipment which can be used to estimate the degree of oxygen saturation of arterial blood. More specifically, the present invention provides an effective noninvasive reflectance oximeter capable of providing accurate readings at lower levels of oxygen saturation.

BACKGROUND

In many clinical situations, it is extremely desirable to be able to obtain continuous measurements of tissue oxygenation. While it is desirable to have an absolute measure of OS, it is often sufficient to measure relative changes in the blood oxygen saturation. For example, in the operating room, the physician is typically concerned only with significant changes in the patient's OS, and is less concerned with the measurement of absolute OS. In this situation, a noninvasive oximeter which is capable of detecting significant changes in the blood oxygen content would be especially useful.

It is well known that hemoglobin and oxyhemoglobin have different optical absorption spectra and that this difference in absorption spectra can be used as a basis for an optical oximeter. Most of the currently available oximeters using optical methods to determine blood oxygen saturation are based on transmission oximetry. These devices operate by transmitting light through an appendage such as a finger or an earlobe. By comparing the characteristics of the light transmitted into one side of the appendage with that detected on the opposite side, it is possible to compute oxygen concentrations. The main disadvantage of transmission oximetry is that it can only be used on portions of the body which are thin enough to allow passage of light. There has been considerable interest in recent years in the development of an oximeter which is capable of using reflected light to measure blood oxygen saturation. A reflectance oximeter would be especially useful for measuring blood oxygen saturation in portions of the patient's body which are not well suited to transmission measurements.

Various methods and apparati for utilizing the optical properties of blood to measure blood oxygen saturation have been shown in the patent literature. Representative devices for utilizing the transmission method of oximetry have been disclosed in U.S. Pat. Nos. 4,586,513; 4,446,871; 4,407,290; 4,226,554; 4,167,331; and 3,998,550. In addition, reflectance oximetry devices and techniques are shown generally in U.S. Pat. Nos. 4,447,150; 4,086,915; and 3,825,342.

A theoretical discussion of a basis for the design of a reflectance oximeter is contained in "Theory and Development of a Transcutaneous Reflectance Oximeter System for Noninvasive Measurements of Arterial Oxygen Saturation," by Yitzhak Mendelson (Published Doctoral Dissertation), No. 8329355, University Microfilms, Ann Arbor, Mich. (1983). A theoretical discussion of the optical properties of blood is found in "Optical Scattering in Blood," by Narayanan R. Pisharoty, (Published Doctoral Dissertation), No. 7124861, University Microfilms, Ann Arbor, Mich. (1971).

Numerous other works have disclosed theoretical approaches for analyzing the behavior of light in blood and other materials. The following is a brief list of some of the most relevant of these references: "New Contributions to the Optics of Intensely Light-Scattering Materials, Part 1," by Paul Kubelka, *Journal of the Optical Society of America*, Volume 38, No. 5, May 1948; "Optical Transmission and Reflection by Blood," by R. J. Zdrojkowski and N. R. Pisharoty, *IEEE Transactions on Biomedical Engineering*, Vol. BME-17, No. 2, April 1970; and "Optical Diffusion in Blood," by Curtis C. Johnson, *IEEE Transactions on Biomedical Engineering*, Vol. BME-17, No. 2, April 1970.

One of the difficulties which has been encountered in the use of optical oximeters is the calibration of such devices to provide accurate readings at lower levels of oxygen saturation. In particular, difficulties have been encountered in the use of optical oximeters to measure oxygen saturations below 90%. The noninvasive reflectance oximeter provided by the present invention overcomes these difficulties, as described in greater detail below.

SUMMARY OF THE INVENTION

The present invention provides a noninvasive reflectance oximeter which is capable of providing accurate indications of a patient's blood oxygen saturation. In the preferred embodiment of the present invention, the blood oxygen saturation of a patient's arterial blood is determined by a noninvasive optical technique which takes advantage of differences in the absorption spectra of hemoglobin and oxyhemoglobin. In its simplest form, the invention comprises means for illuminating the patient's arterial blood with light at two different wavelengths, means for measuring the intensity of the reflected light after contact with the blood and means for correlating the intensity of the reflected light with an oxygen saturation reference curve to determine the oxygen saturation of the patient's blood. One of the sources of light is at a wavelength for which the absorption coefficients of hemoglobin and oxyhemoglobin differ from one another. The reflected light signal detected by the system comprises an alternating-current (AC) component and a direct-current (DC) component for each of the respective light sources. The AC components of each of the reflected signals is filtered from the output of the sensor and a voltage amplitude ratio is calculated. This ratio is then correlated with an oxygen saturation reference curve to obtain an indication of the oxygen saturation of the patient's arterial blood.

The reference curve used in the preferred embodiment of the invention is calibrated in a two-step process which minimizes the effects of calibration errors. A first oxygen saturation reference curve is calculated which is based on a linear relationship between the ratio of the AC components of the reflected light. This curve is then used to calibrate a second reference curve based on a linear ratio of the squared values of the AC components of the reflected light. Once the second reference curve has been properly calibrated, it is used for all subsequent measurements of oxygen saturation.

DETAILED DESCRIPTION OF THE PREFERRED EMBODIMENT

Figure 1:
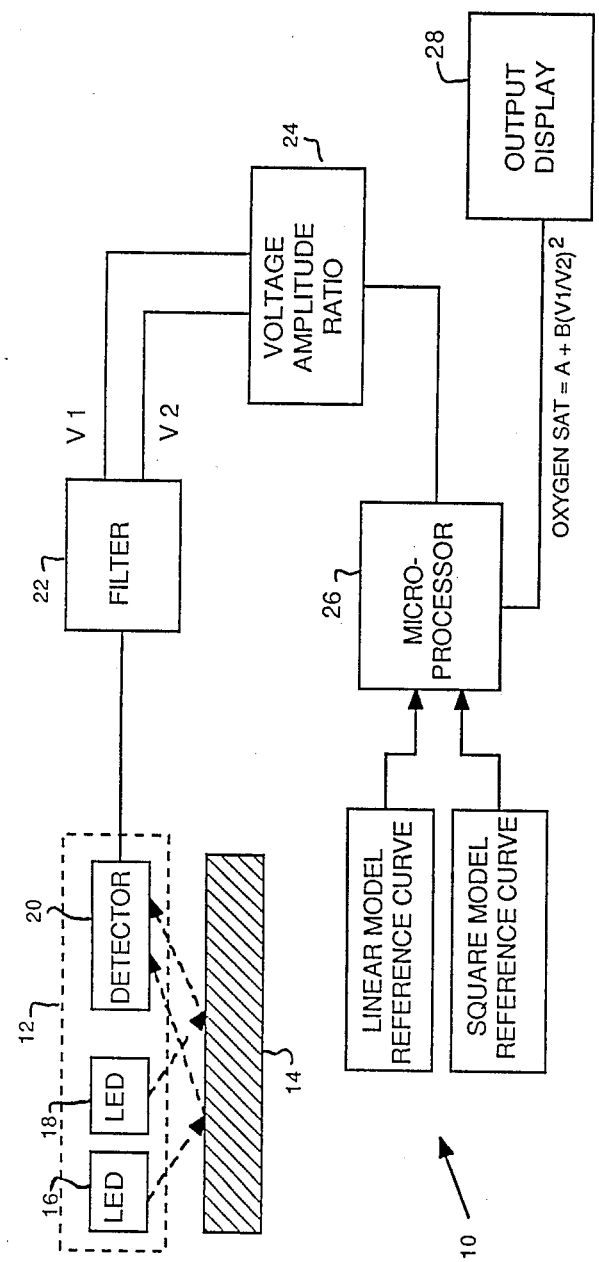
FIG. 1 is a schematic block diagram of a simplified embodiment of the noninvasive blood oxygen saturation monitoring system of the present invention.

Referring to the drawings in more detail, and to FIG. 1 in particular, the noninvasive monitoring system 10 of the present invention is shown in its preferred embodiment. A monitoring probe 12 is positioned over a portion of the patient's tissue 14 such that light produced by two light emitting diodes (LED) 16 and 18 will be reflected by arterial blood in the tissue and detected by a photodetector 20. In the preferred embodiment, the LED 16 emits light having a wavelength of 660 nm (red) and the LED 18 emits light having a wavelength of 900 nm (infrared). However, the invention is not intended to be limited to any specific wavelength of light produced by the above-mentioned LEDs. Proper operation of the invention requires only that one of the sources of light have a wavelength at which the absorption coefficients of hemoglobin and oxyhemoglobin differ from one another. The output of the photodetector 20 will be an electrical signal representing a combination of direct-current (DC) and alternating-current (AC) components of the light reflected by the arterial blood in the tissue 14. This output signal is processed by an appropriate filter 22 to produce signals corresponding to the AC voltage components of each of the wavelengths of incident light. These AC voltage signals are then processed by a voltage amplitude ratio circuit 24 to provide an output signal corresponding to the ratio of the AC portions of the reflected signals. The voltage amplitude ratio output signal is provided to a microprocessor 26 which calculates the oxygen saturation using a Linear Model Reference Curve and a Square Model Reference Curve described in greater detail below. The calculated oxygen saturation is then displayed on an appropriate display device 28.

The use of the AC component of the reflected signal offers significant advantages for correlating the signals with blood oxygen saturation. As blood volume increases during systole, more light is absorbed by the blood and a decrease in tissue reflectance can be observed. During diastole, tissue blood volume decreases and an increase in the reflected light intensity can be observed. In general, the amplitude ratio of the AC components of the reflected signals will not be significantly affected by fixed light absorbers, such as bone, hair and skin pigmentation.

The techniques used to calculate oxygen saturation in the invention system can be understood from the following discussion of the relationships between the reflected light signals detected by the system. The following equation describes light reflection from a turbid, both absorbing and scattering, medium:

$$R_d = \left(\frac{s + k - q}{s}\right)\left(\frac{1 - e^{-2qd}}{1 - Ae^{-2qd}}\right)$$

$$q = \sqrt{k(k + 2s)}$$

$$A = \frac{s + k + q}{s + k - q}$$

$R_d$—reflection of light from a medium.
d—thickness of the medium.
s—scattering coefficient of medium.
k—absorption coefficient of medium.

For a reflectance oximeter the thickness of the medium can be considered to be very large. Using this assumption, the above equation can be simplified to yield the following relationship:

$$R_\infty = \frac{s + k - q}{s} \text{ at } d = \infty$$

By subtracting the signal at diastolic from the signal at systolic, and using two different wavelengths, the following relationship can be seen:

$$BS_{AC_{red}} = \frac{s_{dred}(k_{sred} - q_{sred}) - s_{sred}(k_{dred} - q_{dred})}{s_{sred} s_{dred}}$$

$$BS_{AC_{ired}} = \frac{s_{dired}(k_{sired} - q_{sired}) - s_{sired}(k_{dired} - q_{dired})}{s_{sired} s_{dired}}$$

where:
$BS_{AC_{red}}$—pulsatile component of backscatter signal for red wavelength.
$BS_{AC_{ired}}$—pulsatile component of backscatter signal for ired wavelength.
$s_{dred}$—scattering coefficient of tissue at diastolic for red wavelength.
$s_{sred}$—scattering coefficient of tissue and arterial blood mixture at systolic for red wavelength.
$k_{dred}$—absorption coefficient of tissue at diastolic for red wavelength.
$k_{sred}$—absorption coefficient of tissue and arterial blood mixture at systolic for red wavelength.
$s_{dired}$—scattering coefficient of tissue at diastolic for ired wavelength.
$s_{sired}$—scattering coefficient of tissue and arterial blood mixture at systolic for ired wavelength.
$k_{dired}$—absorption coefficient of tissue at diastolic for ired wavelength.
$k_{sired}$—absorption coefficient of tissue and arterial blood mixture at systolic for ired wavelength.

Dividing the red value by the infrared value gives the following equation for the measured ratio, r:

$$r = \frac{BS_{AC_{red}}}{BS_{AC_{ired}}}$$

It has been determined that a linear relationship exists between the measured ratio, r, and oxygen saturation. This relationship, hereafter referred to as the Linear Model, can be expressed as follows:

$$OS = A_{lin} + B_{lin} r$$

where:
OS—Oxygen Saturation.
$A_{lin}$—intercept of Linear Model regression line.
$B_{lin}$—slope of Linear Model regression line.

The intercept of the Linear Model, $A_{lin}$, can be calculated as follows:

$$r = \frac{BS_{AC_{red}}}{BS_{AC_{ired}}} = 0 \text{ at } OS = A_{lin}$$

$$BS_{AC_{red}} = 0 \text{ at } r = 0$$

Simplification of the above equation yields the following equations:

$$k_{sred} = \frac{k_{dred}s_{red}}{s_{dred}}$$

$$(1 - v_a)k_{dred} + v_a k_{ared} = \frac{k_{dred}s_{red}}{s_{dred}}$$

$$(1 - v_a)k_{dred} + v_a k_{ared} = \frac{k_{dred}((1 - v_a)s_{dred} + v_a s_{ared})}{s_{dred}}$$

$$k_{ared} = \frac{k_{dred}s_{ared}}{s_{dred}}$$

$$k_{ared} = C_{Hb}(OS(HbO2_{red} - Hb_{red}) - Hb_{red}) = \frac{k_{dred}s_{ared}}{s_{dred}}$$

Therefore:

$$A_{lin} = \frac{S_{ared}k_{dred}}{C_{Hb}S_{dred}(HbO2_{red})} - \frac{Hb_{red}}{HbO2_{red} - Hb_{red}}$$

where:
$k_{ared}$—absorption coefficient of arterial blood for red wavelength.
$s_{ared}$—scattering coefficient of arterial blood for red wavelength.
$v_a$—change in tissue volume due to arterial blood.
$HbO2_{red}$—absorption coefficient of oxygenated hemoglobin for red wavelength.
$Hb_{red}$—absorption coefficient of reduced hemoglobin for red wavelength.
$C_{Hb}$—concentration of hemoglobin in the arterial blood.

The first term in the equation for the intercept, $A_{lin}$, is very samll in comparison to the second term. Thus the first term can be eliminated with very little error. The equation can thus be simplified as follows:

$$A_{lin} = \frac{Hb_{red}}{Hb_{red} - HbO2_{red}}$$

The term $A_{lin}$ is composed of the absorption coefficients for oxygenated and reduced hemoglobin at a known wavelength, for example 660 nm (red). These values are known constants which are related to the wavelength of light used to illuminate the blood. Therefore, the Y-intercept can be calculated by substituting the values of these absorption coefficients. As an example, for light at 660 nm, the Y-intercept is calculated to be a hypothetical value of 113%. While this point has no physical meaning, experimental data has shown that the hypothetical Y-intercept, $A_{lin}$ tends to be fairly constant for different individuals. The slope of the regression curve, however, tends to vary for different individuals. Therefore, the slope of the Linear Model, $B_{lin}$, is determined by calibrating the system to a patient at a known oxygen saturation value, e.g. 98%. Given a known oxygen saturation and a corresponding measured voltage ratio, the slope, $B_{lin}$, can be calculated as follows:

$$B_{lin} = \frac{OS - A_{lin}}{r}$$

Figure 2:
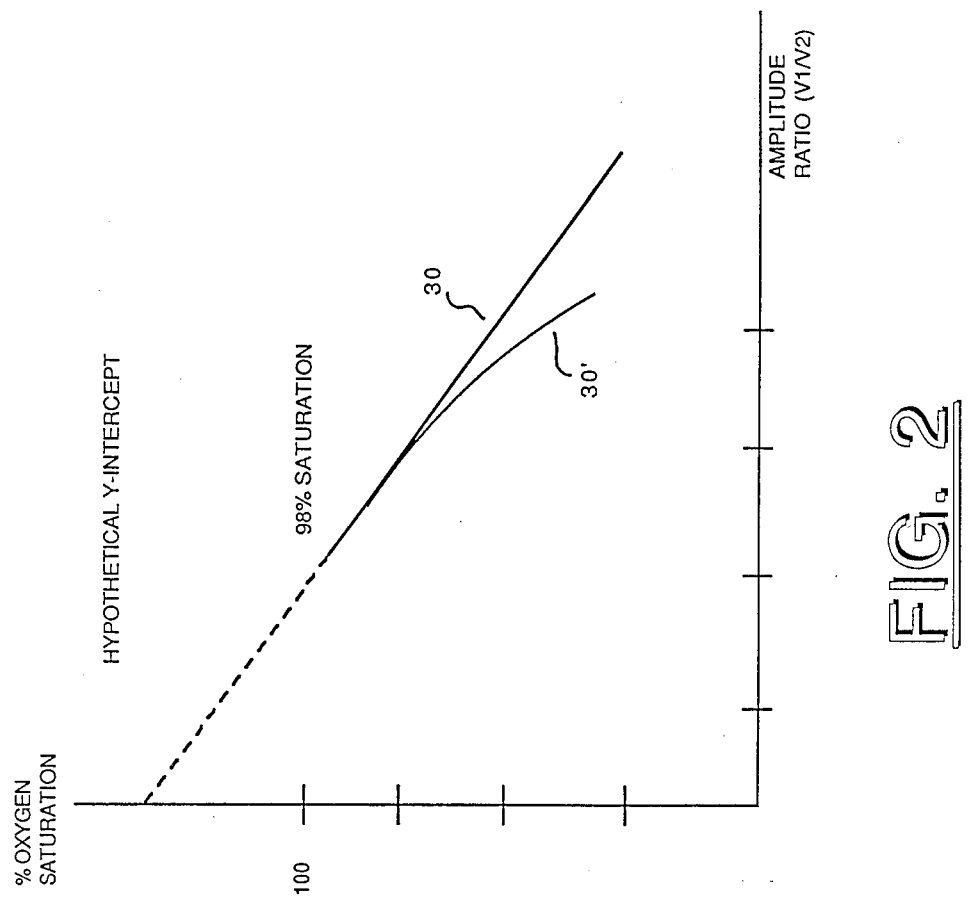
FIG. 2 is a graphical representation of a linear oxygen saturation curve provided by the monitoring system shown in FIG. 1.

FIG. 2 is a graphical representation of an oxygen saturation reference curve 30 obtained using the Linear Model described above. Empirical data has shown that this model provides an accurate indication of oxygen saturation in the range from 90% to 100%. However, in the lower range of oxygen saturation the readings provided by the Linear Model tend to be inaccurate. It has been determined that oxygen saturation at lower levels can represented by a curve such as 30', which can be defined by the following relationship.

$$OS = A_{sqr} + B_{sqr}r^2$$

where:
$A_{sqr}$—intercept of Square Model regression line.
$B_{sqr}$—slope of Square Model regression line.

Figure 3:
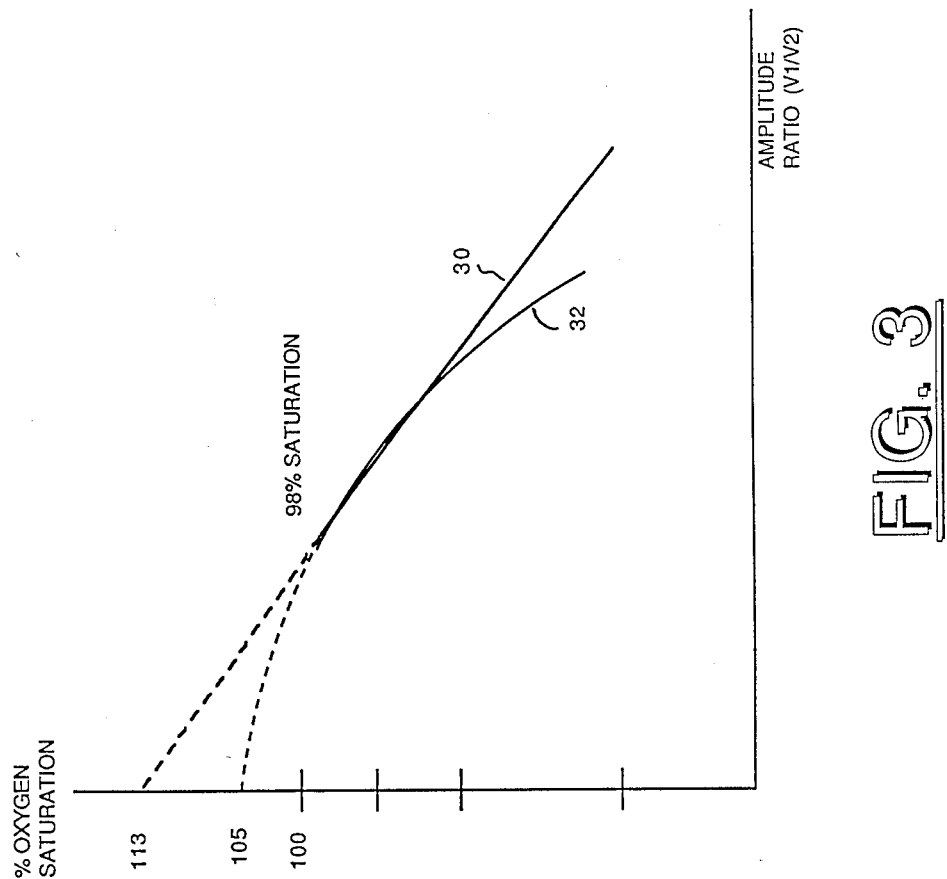
FIG. 3 is a graphical representation of an oxygen saturation reference curves formed by extrapolation techniques using the mathematical relationships provided by the method of the present invention.

This relationship, which hereafter is referred to as the Square Model, can also be used to measure oxygen saturation in the region between 90% and 100%. This is illustrated by the curves 30 and 32 shown in FIG. 3. As can be seen the values of the two curves are approximately the same in the region between 90% and 100%. The slope and intercept of the Square Model can be calculated by incorporating the assumptions regarding the similarities of the Models in this region into the equation for the Square Model, as shown below:

$$OS_1 = A_{lin} + B_{lin}r_1$$

$$OS_2 = A_{lin} + B_{lin}r_2$$

$$OS_1 = A_{sqr} + B_{sqr}r_1^2$$

$$OS_2 = A_{sqr} + B_{sqr}r_2^2$$

where:
$OS_1$—98% oxygen saturation.
$OS_2$—92% oxygen saturation.
$r_1$—the value of the linear ratio at $OS_1$.
$r_2$—the value of the linear ratio at $OS_2$.

Using the above equations, the Square Model can be solved for the intercept, $A_{sqr}$, as follows:

$$A_{sqr} = OS_2 - B_{sqr}r_2^2$$

$$B_{sqr} = \frac{OS_1 - OS_2}{r_1^2 - r_2^2}$$

$$A_{sqr} = OS_2 - \frac{(OS_1 - OS_2)r_2^2}{r_1^2 - r_2^2}$$

$$r_1 = \frac{OS_1 - A_{lin}}{B_{lin}}$$

$$r_2 = \frac{OS_2 - A_{lin}}{B_{lin}}$$

$$A_{sqr} = OS_2 - \frac{(OS_2 - A_{lin})^2}{OS_1 + OS_2 - 2A_{lin}}$$

$$A_{sqr} = OS_2 - \frac{\left(OS_2 - \frac{Hb_{red}}{Hb_{red} - HbO2_{red}}\right)^2}{OS_1 + OS_2 - \frac{2Hb_{red}}{Hb_{red} - HbO2_{red}}}$$

Using the above equations, the Square Model can be solved for the slope, $B_{sqr}$, as follows:

$$B_{sqr} = \frac{OS_2 - A_{sqr}}{r_2^2}$$

-continued $$B_{sqr} = \frac{OS_2 - OS_2 + \frac{(OS_2 - A_{lin})^2}{OS_1 + OS_2 - 2A_{lin}}}{\frac{(OS_2 - A_{lin})^2}{B_{lin}^2}}$$

$$B_{sqr} = \frac{B_{lin}^2}{OS_1 + OS_2 - 2A_{lin}}$$

$$B_{sqr} = \frac{B_{lin}^2}{OS_1 + OS_2 - \frac{2Hb_{red}}{Hb_{red} - HbO2_{red}}}$$

Therefore:

$$A_{sqr} = OS_2 - \frac{\left(OS_2 - \frac{Hb_{red}}{Hb_{red} - HbO2_{red}}\right)^2}{OS_1 + OS_2 - \frac{2Hb_{red}}{Hb_{red} - HbO2_{red}}}$$

$$B_{sqr} = \frac{B_{lin}^2}{OS_1 + OS_2 - \frac{2Hb_{red}}{Hb_{red} - HbO2_{red}}}$$

$$OS = A_{sqr} + B_{sqr}r^2$$

By substituting the appropriate known constants into the equation for the Y-intercept for the Square Model, $A_{sqr}$, can be calculated. For example, the $A_{sqr}$ for light at a wavelength of 660 nm can be calculated to be approximately 105%. The slope, $B_{sqr}$, of the Square Model curve can then be calculated by measuring an actual oxygen saturation data point for a particular individual, e.g., 98%, and using the mathematical relationships discussed above.

Referring again to FIG. 3, it can be seen that the Linear Model reference curve 30 and the Square Model reference curve 32 will provide very similar oxygen saturation readings in the range from 90% to 100%. Therefore, either of these reference curves can be used to provide accurate readings in this range. However, as discussed above, the Square Model reference curve 32 will provide more accurate readings in the range below 90%. Since the Square Model reference curve can be used to provide accurate readings in both the upper and lower ranges of the curve, it would be desirable to use this single reference curve for all oxygen saturation measurements.

One of the difficulties encountered in the use of the Square Model reference curve is related to the calibration of the curve. In particular, the hypothetical Y-intercept, $A_{sqr}$, and the actual oxygen saturation point used to construct the curve are typically very close together, e.g., 105% and 98%. A small error in the determination of the voltage ratio corresponding to the 98% point can lead to a significant error in the lower ranges of the curve after extrapolating downward. This problem has been overcome in the present invention by first calibrating the system with the Linear Model reference curve, which is less susceptible to propogation of error. Once the linear reference curve has been calculated, the oxygen saturation for a point in the vicinity of 90% is calculated and this data point is used to calibrate the Square Model reference curve. Once the Square Model reference curve has been calibrated, it is used for all subsequent calculations of oxygen saturation.

The two step calibration technique used in the preferred embodiment can be summarized as follows: A first data point $A_{lin}$ is calculated using absorption coefficients for oxygenated and reduced hemoglobin at a known wavelength. For the wavelengths of light used in the preferred embodiment, the value of $A_{lin}$ will be a hypothetical value of approximately 113%. A second data point is then obtained by measuring an actual oxygen saturation point for a particular individual. In the preferred embodiment, the second data point is measured at approximately 98%, although other saturation levels could be used without departing from the principles of the present invention. Using these two data points, the slope, $B_{lin}$, of the Linear Model reference curve can be calculated and the linear reference curve can be formed. This reference curve is then used to calculate a third data point corresponding to an oxygen saturation in the vicinity of 90% (e.g., between 88 and 92%). A fourth data point corresponding to the Y-intercept, $A_{sqr}$ of the Square Model reference curve is then calculated using absorption coefficients for oxygenated and reduced hemoglobin at a known wavelength. In the preferred embodiment, this fourth data point is a hypothetical value of approximately 105%. Using these third and fourth data points, the slope, $B_{sqr}$, of the Square Model reference curve is calculated and the square reference curve is formed. Once this curve has been formed, it is used for all subsequent measurements of oxygen saturation.

While the invention method and apparatus for noninvasive monitoring of arterial blood oxygen saturation has been described in connection with the preferred embodiment, it is not intended to be limited to the specific form set forth herein, but on the contrary, it is intended to cover such alternatives, modifications and equivalents as may be reasonably included within the spirit and scope of the invention as defined by the appended claims.

We claim:

1. A blood oxygen saturation monitoring system comprising:
    a first source of electromagnetic radiation at a first wavelength;
    a second source of electromagnetic radiation at a second wavelength;
    means for positioning said first and second sources of electromagnetic radiation to illuminate a sample of blood;
    sensing means for receiving electromagnetic radiation reflected by said sample of blood, said reflected electromagnetic radiation comprising an AC component and a DC component, said sensing means producing an output signal corresponding only to the AC components of the reflected portions of said first and second electromagnetic radiation;
    means for producing a quotient of squared values of said AC voltage components;
    means for calculating blood oxygen saturation by correlating said quotient of said squared AC components with an oxygen saturation reference curve, said reference curve being uniquely representative of the blood oxygen saturation characteristics of a particular individual.

2. The monitoring system according to claim 1, wherein said first and second sources of electromagnetic radiation comprise first and second light emitting diodes.

3. The monitoring system according to claim 2, wherein said first light emitting diode provides light having a wavelength corresponding to red and said second light emitting diode provides light having a wavelength corresponding to infrared.

4. The monitoring system according to claim 3, wherein said first reference curve is defined by first and second data points, said first data point comprising a quotient calculated using optical properties of blood for said first wavelength, said second data point being a unique oxygen saturation point for said particular individual.

5. The monitoring system according to claim 4, wherein said first data point is defined by a quotient comprising values for the absorption coefficient for reduced hemoglobin for red light and the absorption coefficient for oxygenated hemoglobin for red light.

6. The monitoring system according to claim 5, wherein said second data point is defined by a unique blood oxygen saturation point for said particular individual.

7. A blood oxygen saturation monitoring system comprising:
   a first light emitting diode for producing light at a first wavelength;
   a second light emitting diode for producing light at a second wavelength;
   means for positioning said first and second light emitting diodes to illuminate a sample of blood;
   sensing means for receiving light reflected by said sample of blood, said reflected light comprising an AC component and a DC component, said sensing means producing an output signal corresponding only to the AC components of said reflected light at said first and second wavelengths;
   means for calculating a first reference curve comprising a linear relationship between the ratio of said AC voltage components, said reference curve being defined by first and second data points, said first data point corresponding to a quotient of absorption coefficients of light at said first wavelength, said second data point being a unique data point corresponding to oxygen saturation characteristics of a particular individual;
   means for calculating a second reference curve defined a linear relationship between squared values of said AC voltage components, said second reference curve being defined by third and fourth data points, said third data point being a data point calculated using said first reference curve, said fourth data point being defined by a quotient of absorption coefficients of light at said first wavelength; and
   means for calculating blood oxygen saturation by correlating said quotient of said squared values of said AC voltage components with said second oxygen saturation reference curve.

8. The monitoring system according to claim 7, wherein said third data point is in the range of 88 to 92 percent oxygen saturation.

9. The monitoring system according to claim 8, wherein said first light emitting diode provides light having a wavelength corresponding to red and said second light emitting diode provides light having a wavelength corresponding to infrared.

10. The monitoring system according to claim 9, wherein said first wavelength of light is approximately 660 nm and said second wavelength of light is approximately 900 nm.

11. The monitoring system according to claim 9, wherein said first data point is defined by a quotient comprising values for the absorption coefficient for reduced hemoglobin for red light and the absorption coefficient for oxygenated hemoglobin for red light.

12. The monitoring system according to claim 11, wherein said second data point is defined by a unique 98% blood oxygen saturation point for said particular individual.

13. A method for determining the oxygen saturation of arterial blood, comprising the steps of:
    illuminating a sample of said blood with electromagnetic radiation at a first wavelength;
    illuminating said sample of blood with electromagnetic radiation at a second wavelength;
    collecting electromagnetic radiation reflected by said sample of blood, said radiation comprising an AC and a DC component, and developing therefrom an electrical signal representing only the alternating current components of said reflected radiation at said first and second wavelengths;
    calculating a first reference curve comprising a linear relationship between the ratio of said AC voltage components, said reference curve being defined by first and second data points, said first data point corresponding to a quotient of absorption coefficients of light at said first wavelength, said second data point being a unique data point corresponding to oxygen saturation characteristics of a particular individual;
    calculating a second reference curve defined a linear relationship between squared values of said AC voltage components, said second reference curve being defined by third and fourth data points, said third data point being a data point calculated using said first reference curve, said fourth data point being defined by a quotient of absorption coefficients of light at said first wavelength; and
    calculating blood oxygen saturation by correlating said quotient of said squared values of said AC voltage components with said second oxygen saturation reference curve.

14. The method according to claim 13, wherein said third data point is in the range of 88 to 92 percent oxygen saturation.

15. The method according to claim 14, wherein said radiation at said first and second wavelengths is produced by first and second light emitting diodes, respectively.

16. The method according to claim 15, wherein said first and second wavelengths of light are approximately 660 nm and 900 nm, respectively.

17. The method according to claim 16, wherein said first data point is defined by a quotient comprising values for the absorption coefficient for reduced hemoglobin for red light and the absorption coefficient for oxygenated hemoglobin for red light.

18. The monitoring system according to claim 17, wherein said second data point is defined by a unique 98% blood oxygen saturation point for said particular individual.

* * * * *